United States Patent [19]
Mylroie

[11] Patent Number: 5,886,189
[45] Date of Patent: *Mar. 23, 1999

[54] MANUFACTURE OF AROMATIC AMINES

[75] Inventor: Victor LaVonne Mylroie, Fairport, N.Y.

[73] Assignee: Eastman Kodak Company, Rochester, N.Y.

[*] Notice: The portion of the term of this patent subsequent to May 29, 2006, has been disclaimed.

[21] Appl. No.: 982,141

[22] Filed: Nov. 25, 1992

Related U.S. Application Data

[63] Continuation of Ser. No. 473,006, Jan. 31, 1990, abandoned.

[51] Int. Cl.$^6$ ...................... C07D 249/16; C07D 231/20
[52] U.S. Cl. ...................... 548/262.4; 548/370.1
[58] Field of Search ............... 548/262.4, 370.1

[56] References Cited

U.S. PATENT DOCUMENTS

| | | | |
|---|---|---|---|
| 3,862,911 | 1/1975 | Chabert | 252/470 |
| 3,997,478 | 12/1976 | Petro | 252/470 |
| 4,224,249 | 9/1980 | Kunz et al. | 260/580 |
| 4,248,962 | 2/1981 | Lau | 430/382 |
| 4,609,620 | 9/1986 | Postle et al. | 430/554 |
| 4,721,811 | 1/1988 | Sherwin et al. | 564/491 |
| 4,792,626 | 12/1988 | Becher et al. | 564/422 |
| 4,882,266 | 11/1989 | Kawagishi et al. | 430/546 |
| 4,929,737 | 5/1990 | Lenz et al. | 548/365 |
| 4,948,722 | 8/1990 | Harder | 430/558 |

FOREIGN PATENT DOCUMENTS

| | | |
|---|---|---|
| 0284240 | of 0000 | European Pat. Off. . |
| 0 321 219 | 6/1989 | European Pat. Off. . |
| 0 423 587 A1 | 10/1989 | European Pat. Off. . |

OTHER PUBLICATIONS

Chemical Abstracts, 87:167196b, 90:87158n, and 92:163351d.
"The Raney Catalyst Family", W. R. Grace & Co. brochure.
Horner et al, "Hydrogen transfer, etc" CA 105: 114375t (1986).

*Primary Examiner*—Patricia L. Morris
*Attorney, Agent, or Firm*—Robert A. Gerlach

[57] ABSTRACT

Sulfur-contaminated aromatic nitro compounds are hydrogenated in the presence of a chrominum-containing Raney cobalt catalyst to corresponding primary amino compounds which are useful as intermediates for photographic dye-forming couplers and for other purposes.

13 Claims, No Drawings

MANUFACTURE OF AROMATIC AMINES

This application is a continuation of application Ser. No. 07/473,006, filed Jan. 31, 1990 now abandoned.

FIELD OF THE INVENTION

This invention relates to the manufacture of aromatic amino compounds which are useful as intermediates for photographic dye-forming couplers and for other purposes and, more particularly, to a method for making such compounds by catalytic hydrogenation of corresponding aromatic nitro compounds.

BACKGROUND

To synthesize aromatic primary amino compounds a desirable method is to hydrogenate corresponding aromatic nitro compounds in the presence of a hydrogenation catalyst. For some of these reactions a wide selection of catalysts is available. A problem arises, however, if the precursor composition, i.e., the aromatic nitro compound, contains sulfur. Even a small amount of sulfur as a contaminant or as a component of the precursor will quickly inactivate the catalyst or, as commonly stated, will poison it.

To remove sulfur that may be present in the precursor composition is expensive and often ineffective since even small amounts of unremoved sulfur will still poison the catalyst. This has been an obstacle to the economical synthesis of certain aromatic amino compounds which are used for making dye-forming couplers for color photography inasmuch as their precursor nitro compounds are made from sulfur-containing compounds. Although the pure nitro compounds themselves contain no sulfur, the reaction product in which they are obtained, unavoidably contains substantial amounts of sulfur which is extruded from sulfur-containing precursors. Even with careful recrystallization, the purified nitro compound may contain from 500 to 50,000 parts by weight per million (ppm) of sulfur, calculated as elemental sulfur. The sulfur may be present as elemental sulfur or as sulfur compounds. In either event the sulfur will poison the types of catalysts which have heretofore been considered to be sufficiently active and selective for hydrogenating nitro-substituted aromatic compounds to corresponding primary amines.

BRIEF SUMMARY OF THE INVENTION

In accordance with the present invention certain catalysts have been found to be unexpectedly successful in hydrogenating sulfur-contaminated aromatic nitro compounds to aromatic primary amines. In the method of the invention, the catalyst is selective for production of the desired product. Hydrogenation of the precursor to unwanted by-products is minimized and the catalyst remains active notwithstanding the presence of sulfur in the reaction mixture.

The method of the invention comprises producing an aromatic primary amine of the formula, R—Ar—NH$_2$, by hydrogenating a sulfur-contaminated nitro compound of the formula, R—Ar—NH$_2$, in the presence of a chromium-containing Raney cobalt catalyst. In the formulae, —Ar— is an arylene radical and R— is a radical selected from the group consisting of Het—, Het—NH—, Het—Alk— and Het—Alk—O—, wherein Het— is a mono- or bi-cyclic nitrogen-containing unsaturated heterocyclic radical, and —Alk— is a straight or branched chain alkylene radical of up to about 15 carbon atoms.

DETAILED DESCRIPTION

The amino compounds made by the method of the invention, which are of the formula R—Ar—NH$_2$, include a class of compounds of the formula

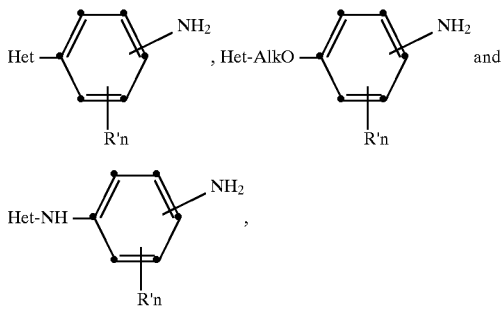

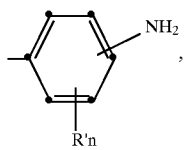

wherein —AlkO— is an alkyleneoxy group such as

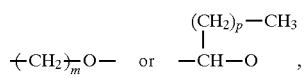

m being from 1 to 15 and p being from 0 to 13. In the radical,

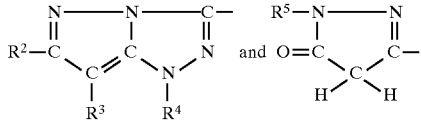

R' is lower alkyl and n is 0 to 4. Examples of such radicals include

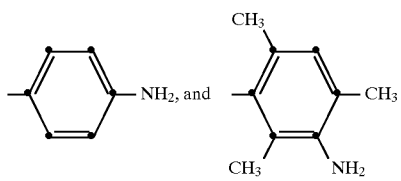

In the formula, R—Ar—NH$_2$, the arylene radical —Ar— can also be a naphthylene radical which is either unsubstituted or substituted as indicated for the phenylene radical.

Examples of the heterocyclic radical, Het—, include wherein R$^2$=hydrogen, lower alkyl, e.g., methyl, t-butyl; higher straight or branched chain alkyl groups of up to about 30 carbon atoms; or aryl, e.g. phenyl. R$^3$=hydrogen, lower alkyl or halogen, e.g., chlorine. R$^3$ can also include other "coupling off" groups useful in photographic couplers provided they do not adversely affect the hydrogenation reaction. R$^4$=hydrogen or lower alkanoyl, e.g., acetyl or butyryl and R$^5$=phenyl or phenyl substituted with lower alkyl or halogen.

The aromatic amino compounds which can be made by the method of the invention thus include a wide range of pyrazolo azoles, especially pyrazolo triazoles, having an aminoaryl group attached either directly to a ring carbon atom of the azole ring or attached by way of an alkylene or oxyalkylene linking group.

The aromatic amino compounds also include a wide range of aminoaryl-substituted pyrazolones which are also useful as dye-forming couplers.

Examples of pyrazolo azole compounds which can be made by the method of the invention are disclosed in European Patent Application 0284240, published 28 Sep. 1988, and U.S. Pat. No. 4,777,121 dated Oct. 11, 1988. Examples of pyrazolones are disclosed in Research Disclosure 308,119 dated December 1989, especially Section VII-D thereof. These and other references cited herein are incorporated by reference.

As is known (see, for example, the above-cited European Patent Application and U.S. Pat. No. 4,777,121) the function of the primary amino group in the compounds produced by the method of the present invention is to provide a site for the addition of a ballast group. Such high molecular weight ballast groups keep the resulting coupler, and the dye which is formed during photographic processing, from migrating from one layer to another in a multilayered photographic film or paper. The formation of primary aromatic amino groups without reducing other portions of the molecules is, therefore, of considerable importance in color photography as well as in other fields.

In the method of the invention the primary amino compounds are made by selectively hydrogenating precursor nitro compounds which are identical to the product compounds except that they have a nitro radical attached to an aromatic nuclear carbon atom where the product has a primary amino radical. Thus, in the method of the invention the nitro group is selectively hydrogenated to a primary amino group without hydrogenating other portions of the precursor compound to any substantial extent.

An outstanding advantage of the new method is that the hydrogenation reaction is carried out in high yield in the presence of a catalyst even though the precursor is contaminated with sulfur, a substance which is well-known to poison conventional hydrogenation catalysts. The reason for the contamination with sulfur is that the nitro-substituted precursors are advantageously made from cyclic compounds which themselves contain sulfur as atoms of a heterocyclic nucleus. The reaction producing the nitro compounds, which are direct precursors for the method of the present invention, extrudes sulfur from an aromatic heterocycle to form a five-membered-ring nitrogen heterocycle. This type of reaction is disclosed, for example, in European Patent application 0284240.

A typical reaction sequence for producing an aromatic nitro compound precursor for the method of the present invention is as follows:

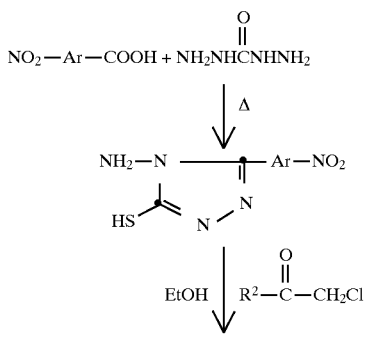

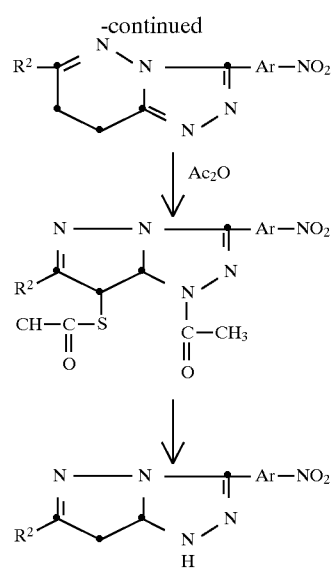

The sulfur-contaminated aromatic nitro compounds made by the above scheme are then hydrogenated by the method of the invention to corresponding aromatic primary amines.

The catalyst which unexpectedly is useful for hydrogenating aromatic nitro compounds in the presence of sulfur is a chromium-promoted Raney cobalt catalyst.

In the method of the invention such catalysts can hydrogenate an aromatic nitro compound at high conversion and yield to the corresponding aromatic amine even though the nitro compound is contaminated with sulfur, e.g., in the range from about 50 to 10,000 ppm. Most frequently, the sulfur contamination will be in the range from about 100 to 5,000 ppm.

The catalyst can be prepared by known procedures used in the preparation of Raney catalysts. An alloy comprising about 50 weight percent aluminum and varying amounts of cobalt, chromium, and, optionally, nickel is prepared, then ground to a desired particle size and finally treated with aqueous sodium hydroxide to extract a portion of the aluminum and thereby activate the catalyst. Typically, after activation the weight ratio of the catalytically active metals, e.g., cobalt, chromium, and, optionally, nickel, to aluminum is in the range of about 7:3 to 8:2.

The chromium-promoted Raney cobalt catalyst used in the hydrogenation process contains about 1 to 10 weight percent chromium, preferably about 2 to 5 weight percent. About 2.5 weight percent is believed to give the best results, i.e., catalytic activity and selectivity. The catalyst may also contain up to about 5 weight percent nickel and preferably contains about 1 to 4, optimumly about 2, weight percent nickel.

The extraction temperature used in the preparation of the active catalyst may be in the range of about 40° to 180° C., preferably in the range of about 60° to 120° C. Catalysts with superior activity are obtained when the extraction temperature is in the range of about 70° to 90° C. There is an apparent correlation between catalyst activity and the amount of cobalt metal, i.e., (Co°) present on the surface of the catalyst. The amount of surface cobalt metal is determined by the equation.

Surface $Co°=[(Co°)/(Co)][(Co)/(Co)+(Cr)][SA]$ wherein (Co°) is cobalt metal, (Co) is total cobalt and (Cr) is total chromium at the surface of the catalyst as determined by electron spectroscopy using a PHI Model 550 ESCA/SAM spectrometer and SA is the BET surface area in square meters per gram using a Model QS11 surface area analyzer made by Quantichrome Co. Factors which give high surface Co° values are the use of a lower extraction temperature in activating the catalyst and the presence of low amounts of chromium.

The amount of catalyst used in the process can be varied substantially depending on several factors such as, for example, the activity of the particular catalyst, the reaction conditions, i.e., temperature and pressure, employed, the reaction time required, the nitroaromatic compound to be hydrogenated and the mode of operation employed. While catalyst concentrations in the range of 0.01 to 10.0 percent based on the weight of the nitroaromatic reactant may be used, normally the concentration will be in the range of about 0.1 to 5.0 percent.

The hydrogenation conditions of temperature and pressure similarly can be varied over a wide range. For example, temperature and pressure are interdependent to some extent and increasing one may permit the use of lower levels of the other. The particular temperature and/or pressure used can also depend on catalyst concentration, the reactant to be hydrogenated, mode of operation as well as the reaction time that is desired. Temperatures in the range of about 10° to 200° C. may be used with the range of about 25° to 125° C. being preferred. Pressures of 100 to 2,000 psig may be employed although the hydrogenation is more often conducted at pressures in the range of about 100 to 1,500 psig. A pressure of at least 500 psig is preferred and the best results are obtained when using low temperatures, e.g., 50° to 100° C., and high pressures, e.g., 600 to 1500 psig.

When the precursor nitro compound contains an alkoxy group or an alkyleneoxy group such as —AlkO— referred to above, an undesired alkylhydroxy byproduct may be produced if the hydrogen pressure is too low. For hydrogenating such compounds, best results are obtained when the pressure is in the range from about 1000 to 2000 psig.

The hydrogenation process is carried out in an inert solvent for the nitroaromatic reactant. The solvent preferably is a primary or secondary alkanol having up to about 4 carbon atoms, especially methanol, ethanol and isopropanol. Co-solvents such as dimethylformamide, dimethylacetamide and tetrahydrofuran may be used in combination with an alkanol when required by the solubility characteristics of the reactant. The solubility of sparingly soluble reactants which have an acidic hydrogen can be enhanced by including a base in the initial reaction mixture. Other solvents which may be employed include esters such as methyl ethyl acetate, ethers such as tetrahydrofuran and diisopropyl ether and, to a lesser extent, hydrocarbons such as toluene.

The method of the invention can be carried out as a batch process, a semi-continuous process or a continuous process. In batch operation a slurry of the catalyst in an inert solvent in which the reactant has been dissolved is fed to a pressure vessel equipped with means for agitation. The pressure vessel then is pressurized with hydrogen to a predetermined pressure and then is heated to bring the reaction mixture to the desired temperature. After the hydrogenation is complete the reaction mixture is removed from the pressure vessel, the catalyst is separated by filtration and the product is isolated, for example, by crystallization followed by filtration. Continuous operation can utilize a fixed catalyst bed using a larger particle size of catalyst. The catalyst bed may be located in a pressure vessel and a solution of the reactant slowly fed continuously above the bed at elevated temperature and pressure and a solution of the aromatic amine removed at the bottom of the pressure vessel. Another mode of continuous operation utilizes a slurry of catalyst in an agitated pressure vessel which is fitted with a filter leg to permit continuous removal of a solution of product in an inert solvent. In this manner a reactant solution can be continuously fed to and product solution continuously removed from an agitated pressure vessel containing a slurry of the catalyst.

In synthesizing a precursor nitroaromatic compound which contains chlorine or another halogen substituent, the nitro compound may not become contaminated with sulfur during that synthesis. The reason is that, when introducing halogen groups into the nitroaromatic molecules, the sulfur can be oxidized to volatile substances such as sulfur dioxide and, hence, removed. On the other hand, such halogen-containing compounds can later become contaminated with sulfur in various ways. The method of the invention, therefore, includes hydrogenating such sulfur-contaminated halogenated compounds.

In this connection, it should be pointed out that the copending patent application of Lentz et al, Ser. No. 151,726, filed Feb. 3, 1988, discloses the hydrogenation of halonitroaromatic compounds with a chromium-containing Raney cobalt catalyst as used in the method of the present invention. In the Lentz et al application there is no disclosure of sulfur-contaminated reactants and no suggestion that the catalyst will remain active in the presence of sulfur and will selectively hydrogenate in high yields sulfur-contaminated heterocyclic aromatic nitro compounds as disclosed herein.

The method of the invention is further illustrated by the following examples.

Examples of the new method are as follows:

EXAMPLE 1

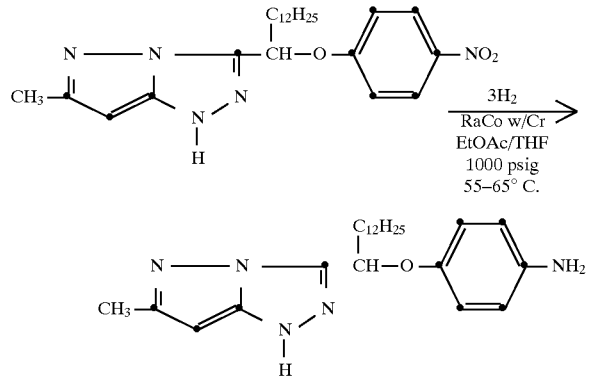

In a catalyst prereduction step, 1000 g (wet weight) of Raney cobalt catalyst containing about 4 weight percent chromium (catalyst supplied by W. R. Grace & Co.) was added to a 25 gallon stainless steel autoclave equipped with stirrer with 37.5 L (33.8 kg) of ethyl acetate. The autoclave was purged with nitrogen twice, then sealed and charged with hydrogen to a pressure of about 500 psig. The autoclave and contents were heated to 50° C. while stirring at about 500 to 800 RPM for one hour. The autoclave and contents were then cooled to 35° to 40° C. and vented of excess hydrogen followed by two complete nitrogen purges. (This prereduction restores the original activity to the catalyst in the event it is not new.) To the open autoclave was added 10 kg of the reactant, 6-methyl-3-(1-(4-nitro-phenoxy)tridecyl)-H-pyrazolo(5,1-c)-1,2,4-triazole (which was contaminated with at least about 500 ppm of sulfur), and 12.5 L of tetrahydrofuran (THF). The autoclave was again purged twice with nitrogen, sealed and then charged with hydrogen to a pressure of 1000 psi and stirred at 55°–65° C. for 30 minutes to 4 hours as required. The reaction was termed complete at the point of no further hydrogen consumption. After that point stirring was continued for about 10 to 15 minutes. The autoclave and contents were then cooled to about 45° C. and the excess hydrogen pressure released and the autoclave purged twice with nitrogen. A sample of the reaction mixture was examined by Thin Layer Chromatography (TLC) on silica gel plates to determine if the reaction was complete. The solvent system for the TLC examination is 9 parts of methylene chloride to 1 part of methanol. Upon completion, the reaction mixture was clarified by filtration to remove the catalyst. The aromatic amine reaction mixture product was now ready for conversion to a magenta dye-forming coupler by reacting the amino group with a ballast molecule, e.g., as described in U.S. Pat. No. 4,777,121. Liq. Chrom. Analysis: 98% amine—off white solid; m.p. 103°–105° C.

In the nomenclature used above, the structure "pyrazolo [5,1-c]-1,2,4-triazole" can also be described as "pyrazolo[3, 2-c]-1,2,4-triazole".

EXAMPLE 2

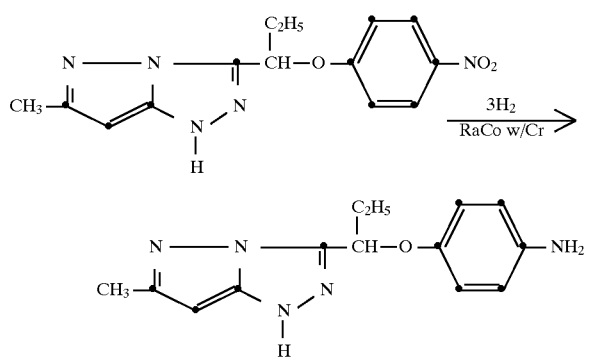

A procedure similar to example 1 was followed to reduce the nitro compound to the corresponding primary amine compound. In this example 80 gm of Raney Cobalt catalyst was prereduced in a 4 L autoclave. The 5 gallon autoclave was then charged 444 g with 6-methyl-3-(1-(4-nitrophenoxy propyl)-1H-pyrazolo(5,1-c)-1,2,4-triazole (contaminated with at least 500 ppm of sulfur) and 5 L of THF. The autoclave was purged twice with nitrogen, sealed and charged with hydrogen to a pressure of 1000 psig and stirred at room temperature to 40° C. for about 5 hours. After the hydrogenation consumption stopped the reaction was continued for about 30 to 60 minutes and then checked for completion by TLC. Upon completion the reaction mixture was clarified to remove the catalyst and recover 6-methyl-3-(1-(4-aminophenoxy)propyl)-1H-pyrazolo(5,1-c)-1,2,4-triazole. Liq. Chrom. Analysis: 99% amine; 90% yield.

Several specific examples of sulfur-contaminated compounds which can hydrogenated by the method of the invention have been disclosed herein. However, the method is useful in general for hydrogenating any nitro-aromatic substituted heterocyclic compounds to corresponding aromatic primary amines when the reactant, i.e., the nitro compound, is contaminated with sulfur and when it is desired to hydrogenate the nitro group selectively without reducing other parts of the molecule such as aromatic rings, unsaturated hetercyclic rings, acyl radicals, alkoxy radicals and the like.

Furthermore, although the method of the invention is especially good for making heterocyclic-aromatic primary amines which are useful as dye-forming photographic coupler intermediates, it can also be used to produce compounds of the formula R—Ar—NH$_2$, having other uses, for example, as pharmaceutical or agricultural chemicals.

EXAMPLE 3

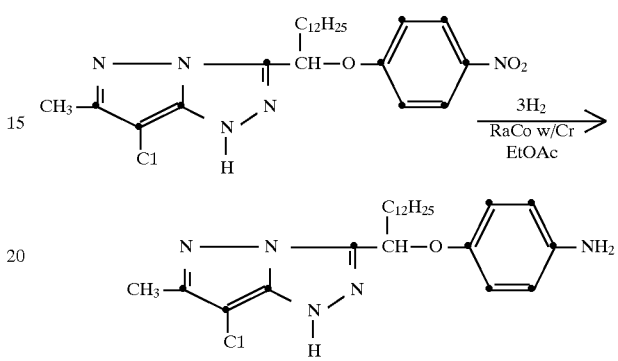

The procedure consisted of charging a 4 L with 40 g (wet weight) of chromium-containing Raney cobalt catalyst and 2000 ml of THF, venting with nitrogen twice and sealing autoclave. The autoclave was charged with hydrogen to 500 psi and heated to 50 degrees C. and stirred at these conditions for 1 hour. The autoclave was vented of excess hydrogen, purged with nitrogen and charged with 377 g (0.933 mole) of the reactant, 7-chloro-6-methyl-3-(1-(4-nitrophenoxy)-tridecyl)-1H-pyrazolo-(5,1-c)-1,2,4-triazole which was contaminated with about 100 ppm of sulfur, and 500 ml of THF, purged with nitrogen, sealed and charged with hydrogen to a pressure of 600 psi. The reaction mixture was stirred at 30 to 35 degrees C. for about 2 hours. At the conclusion of the hydrogenation period the reaction mixture was sampled by TLC to check for completion. Yield, 93.5%; the isolated aromatic amine product being 99% pure by liquid chromatographic analysis.

EXAMPLES 4–6

Other sulfur-contaminated nitroaromatic compounds which have been successfully hydrogenated in accordance with the invention, following procedures similar to those described in Examples 1–3 include the following.

EXAMPLE 4

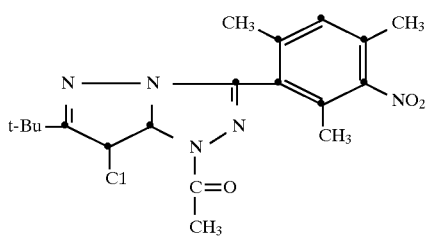

EXAMPLE 5

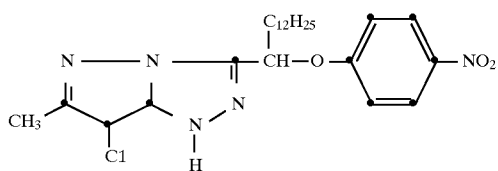

EXAMPLE 6

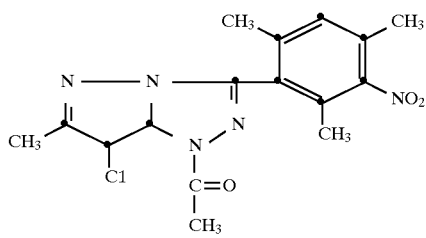

Comparative Examples

In contrast to the results shown in the above examples, the applicant has attempted to use other catalysts such as supported palladium (e.g., palladium on carbon), sulfided supported palladium and supported platinum (e.g., platinum on carbon) for hydrogenating the same or similar sulfur-contaminated aromatic nitro compounds. The sulfur rapidly poisoned these catalysts and to achieve satisfactory yields required removing the catalyst and substituting fresh catalyst in a series of four to six cycles. Applicant has also unsuccessfully attempted to use a Raney nickel catalyst for hydrogenating such aromatic nitro compounds having an alkoxy linkage. The result was cleavage of a phenolic radical from the precursor molecule.

The invention has been described in detail with particular reference to preferred embodiments thereof, but it will be understood that variations and modifications can be effected within the spirit and scope of the invention.

I claim:

1. A method of producing aromatic primary amines of the formula R—Ar—$NH_2$ which comprises catalytically hydrogenating an aromatic nitro compound of the formula R—Ar—$NO_2$ which is derived from a sulfur-containing compound which is contaminated with sulfur, the hydrogenation being carried out in the presence of a chromium-containing Raney cobalt catalyst and wherein R is a radical selected from the group consisting of Het—, Het—NH—, Het—Alk— and Het—Alk—O— and wherein Het— is a mono- or by-cyclic nitrogen-containing unsaturated heterocyclic radical, Alk— being a straight or branched chain alkylene radical of up to about 15 carbon atoms and —Ar— being a phenylene or a naphthylene radical.

2. A method according to claim 1 wherein the hydrogenation conditions include a temperature from about 10° to 100° C. and a pressure up to about 2000 psig.

3. A method according to claim 2 wherein R is Het—Alk—O— and the hydrogenation pressure is at least about 1000 psig.

4. A method according to claim 3 wherein the Raney cobalt catalyst contains 1 to 10 weight percent chromium.

5. A method according to claim 4 wherein the catalyst also contains about 1 to 4 weight percent nickel.

6. A method according to claim 1 wherein Het— is a pyrazolo azole dye-forming coupler radical.

7. A method according to claim 6 wherein Het— is a pyrazolo triazole dye-forming coupler radical.

8. A method according to claim 1 wherein the compound R—Ar—$NO_2$ is contaminated with from about 50 to 10,000 ppm of sulfur.

9. A method according to claim 8 wherein said compound is contaminated with from about 100 to 5,000 ppm of sulfur.

10. A method according to claim 1 wherein Het— is of the formula

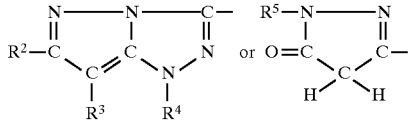

wherein $R^2$=hydrogen, alkyl of up to about 30 carbon atoms or aryl, $R^3$=hydrogen, lower alkyl or halogen; $R^4$=hydrogen or lower alkanoyl; and $R^5$=phenyl or phenyl substituted with lower alkyl or halogen.

11. A method according to claim 1 wherein Het— is a pyrazolone dye-forming coupler radical.

12. A method according to claim 1 wherein said nitro compound is contaminated with sulfur to the extent of at least about 100 ppm of sulfur.

13. A method according to claim 1 wherein said nitro compound is contaminated with sulfur to the extent of about 500 to 5,000 ppm of sulfur.

* * * * *